US006418933B1

(12) United States Patent
Strong

(10) Patent No.: US 6,418,933 B1
(45) Date of Patent: Jul. 16, 2002

(54) ANTI-SNORING DEVICE AND METHOD OF MAKING SAME

(76) Inventor: Patrick J. Strong, 1310 Wigle Grove Road, Kingsville, Ontario (CA), N9Y 3S1

( * ) Notice: Subject to any disclaimer, the term of this patent is extended or adjusted under 35 U.S.C. 154(b) by 0 days.

(21) Appl. No.: 09/881,928

(22) Filed: Jun. 15, 2001

(51) Int. Cl.[7] .................................................. A61F 5/56
(52) U.S. Cl. ...................... 128/848; 128/859; 128/861; 602/902
(58) Field of Search ..................... 128/848, 859–861, 128/863; 433/19, 37, 6; 602/902; A61F 5/56

(56) References Cited

U.S. PATENT DOCUMENTS

| | | | | |
|---|---|---|---|---|
| 5,183,388 A | * | 2/1993 | Kumar ........................... 433/19 |
| 5,499,633 A | | 3/1996 | Fenton .......................... 128/848 |
| 5,562,106 A | * | 10/1996 | Heeke et al. ................ 128/848 |
| 5,601,093 A | * | 2/1997 | Sheehan ....................... 128/848 |
| 5,682,903 A | * | 11/1997 | Meade .......................... 128/848 |
| 5,755,219 A | * | 5/1998 | Thornton ................. 128/201.18 |
| 5,823,193 A | * | 10/1998 | Singer et al. ................ 128/848 |
| 5,941,247 A | * | 8/1999 | Keane .......................... 128/848 |
| 6,041,784 A | * | 3/2000 | Halstrom ..................... 128/848 |
| 6,170,485 B1 | * | 1/2001 | Orrico ......................... 128/848 |

FOREIGN PATENT DOCUMENTS

WO   WO 94/28832   * 12/1994   ............. A61F/5/56

* cited by examiner

*Primary Examiner*—Denise M. Pothier
*Assistant Examiner*—Q D Thanh
(74) *Attorney, Agent, or Firm*—David P. Gordon; David S. Jacobson; Thomas A Gallagher

(57) ABSTRACT

An anti-snoring device has maxillary and mandibular bite forms with outwardly extending pivots which are mounted to the bite forms by frameworks which are at least partially embedded in the bite forms. This retains the pivots securely in place even in the face of extensive bruxing. In constructing the device, a jig may be used for positioning the pivots. The method of manufacturing the device involves casting the frameworks, such that each framework has a pair of pivot mounts, mounting pivots to the pivot mounts, and at least partially embedding the frameworks in the bite forms.

10 Claims, 7 Drawing Sheets

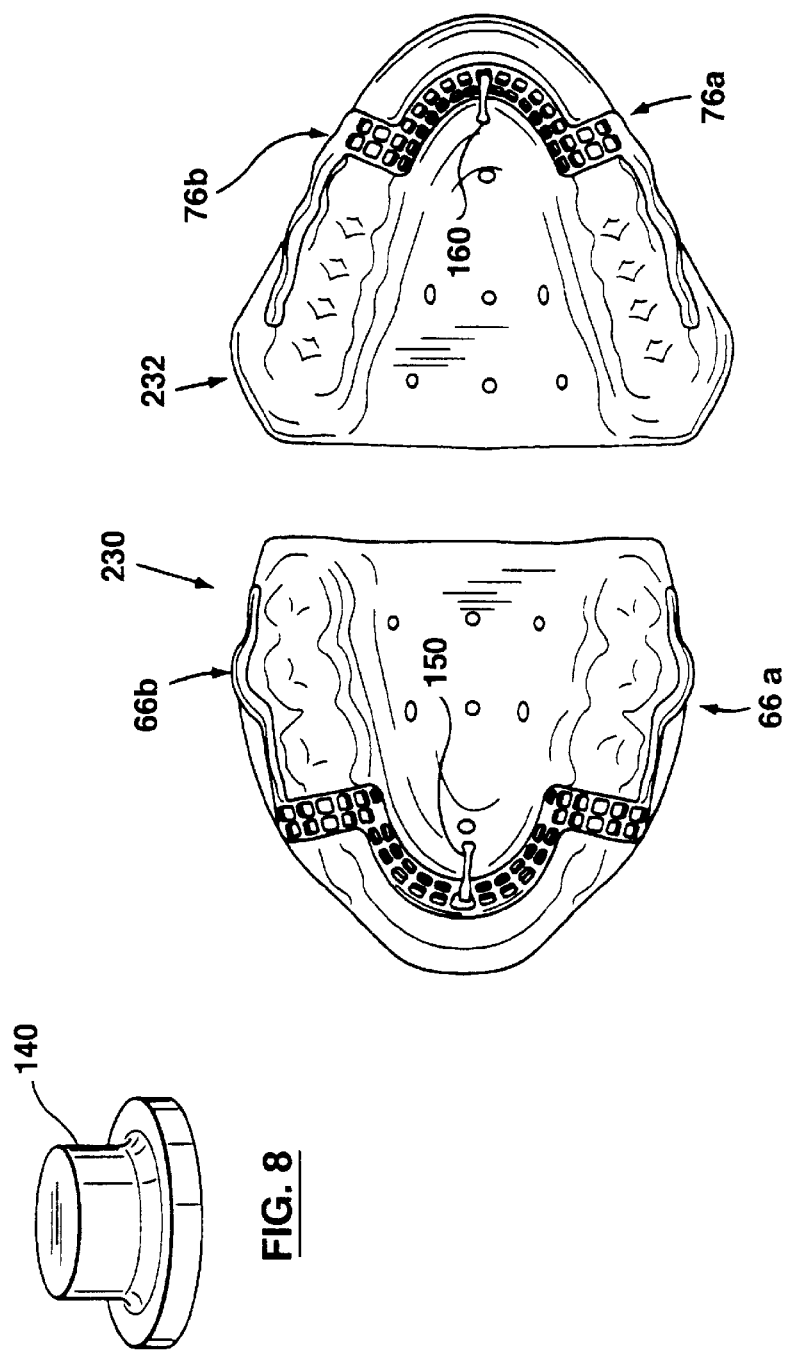

ANTI-SNORING DEVICE AND METHOD OF MAKING SAME

BACKGROUND OF THE INVENTION

Snoring is a common affliction. It results from the muscles holding the mandible (lower jaw) relaxing during sleep such that the mandible moves posteriorly into the throat. This causes the throat to constrict increasing the speed and pressure of inhaled air which vibrates soft tissue in the back of the mouth. For some, who suffer from sleep apnea, the airway becomes completely blocked thereby interrupting breathing during sleep.

Snoring and sleep apnea can be avoided by preventing the mandible from moving posteriorly during sleep. A number of devices have been designed with this purpose in mind. For example, U.S. Pat. No. 5,499,633 to Fenton shows two bite forms which may be joined so that the user's mandible projects forwardly of its normal position in order to reduce snoring.

This invention seeks to provide an improved anti-snoring device and a method of manufacturing same.

SUMMARY OF INVENTION

An anti-snoring device has maxillary and mandibular bite forms with outwardly extending pivots which are mounted to the bite forms by frameworks which are at least partially embedded in the bite forms. This retains the pivots securely in place even in the face of extensive bruxing.

In constructing the device, a jig may be used for positioning the pivots.

The method of manufacturing the device involves casting the frameworks, such that each framework has a pair of pivot mounts, mounting pivots to the pivot mounts, and at least partially embedding the frameworks in the bite forms.

Accordingly, the present invention comprises an anti shoring device, comprising: a maxillary bite form; a mandibular bite form; a first outwardly extending maxillary pivot posteriorly located on a first side of said maxillary bite form; a second outwardly extending maxillary pivot posteriorly located on a second side of said naxillary bite form; a first outwardly extending mandibular pivot anteriorly located on a first side of said mandibular bite form; a second outwardly extending mandibular pivot anteriorly located on a second side of said mandibular bite form; a first telescoping arm loosely pivoted to said first maxillary pivot and to said first mandibular pivot; a second telescoping arm loosely pivoted to said second maxillary pivot and to said second mandibular pivot; maxillary framework at least partially embedded in said maxillary bite form having a pivot mount for said first maxillary pivot and a pivot mount for said second maxillary pivot; mandibular framework at least partially embedded in said mandibular bite form having a pivot mount for said first mandibular pivot and a pivot mount for said second mandibular pivot.

According to another aspect of the present invention, there is provided a jig for positioning of pivots of an anti-snoring device, comprising: a medial portion having an inward face; a first end portion having a pivot receptor canted toward said inward face of said medial portion; a second end portion opposite said first having a plurality of aligned pivot receptors along its length, said pivot receptors canted downwardly.

According to a further aspect of the invention, there is provided a method of manufacturing an anti-snoring device, comprising: casting a maxillary framework and a mandibular framework, such that each framework has a pair of pivot mounts; mounting pivots to said pivot mounts; embedding said maxillary framework at least partially in a maxillary bite form such that pivots extend outwardly from opposite sides of said maxillary bite form, embedding said mandibular framework at least partially in a mandibular bite form such that pivots extend outwardly from opposite sides of said mandibular bite form.

Other aspects and features of the invention will become apparent from the following description.

BRIEF DESCRIPTION OF THE DRAWINGS

In the figures which illustrate example embodiments of the invention,

FIG. 8 is top and side views of a duplicating pivot used in the construction of the device of FIG. 1, FIG. 9 is a top view of maxillary and mandibular framework fabricating casts with maxillary and mandibular frameworks of the device of FIG. 1.

DETAILED DESCRIPTION

Figure 1:
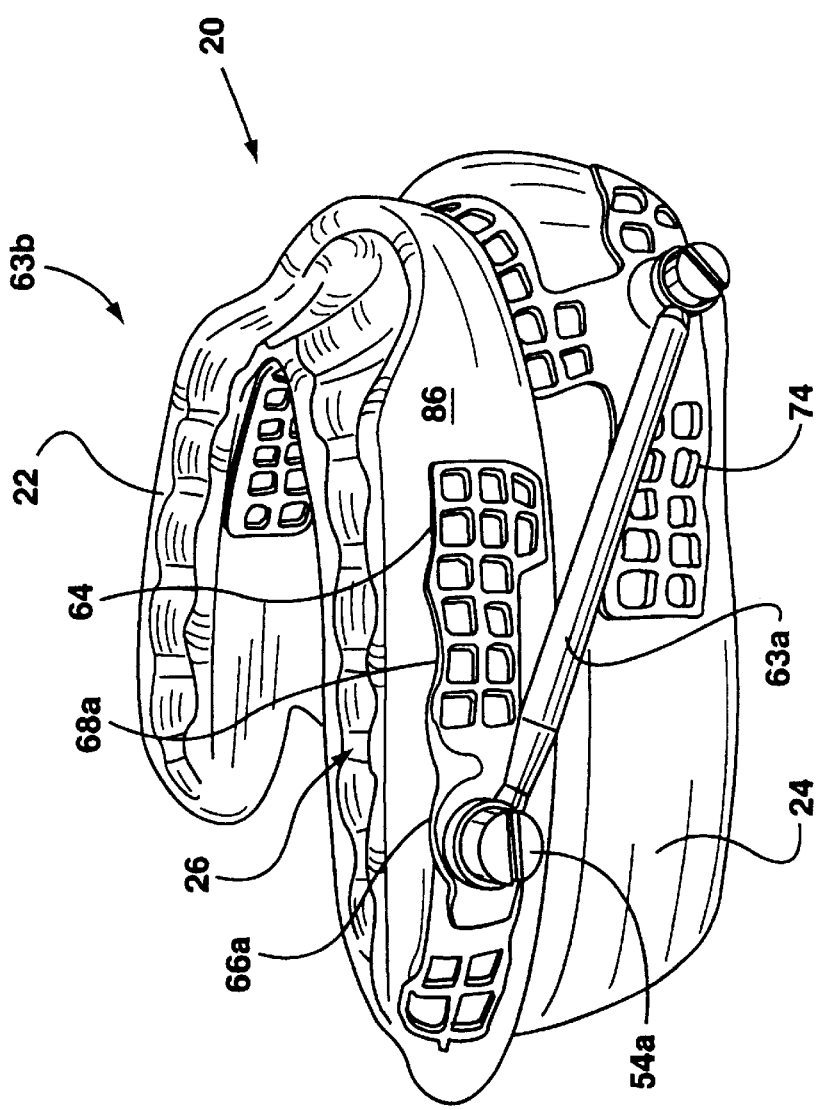
FIG. 1 is a perspective view of a device made in accordance with this invention.
Figure 2:
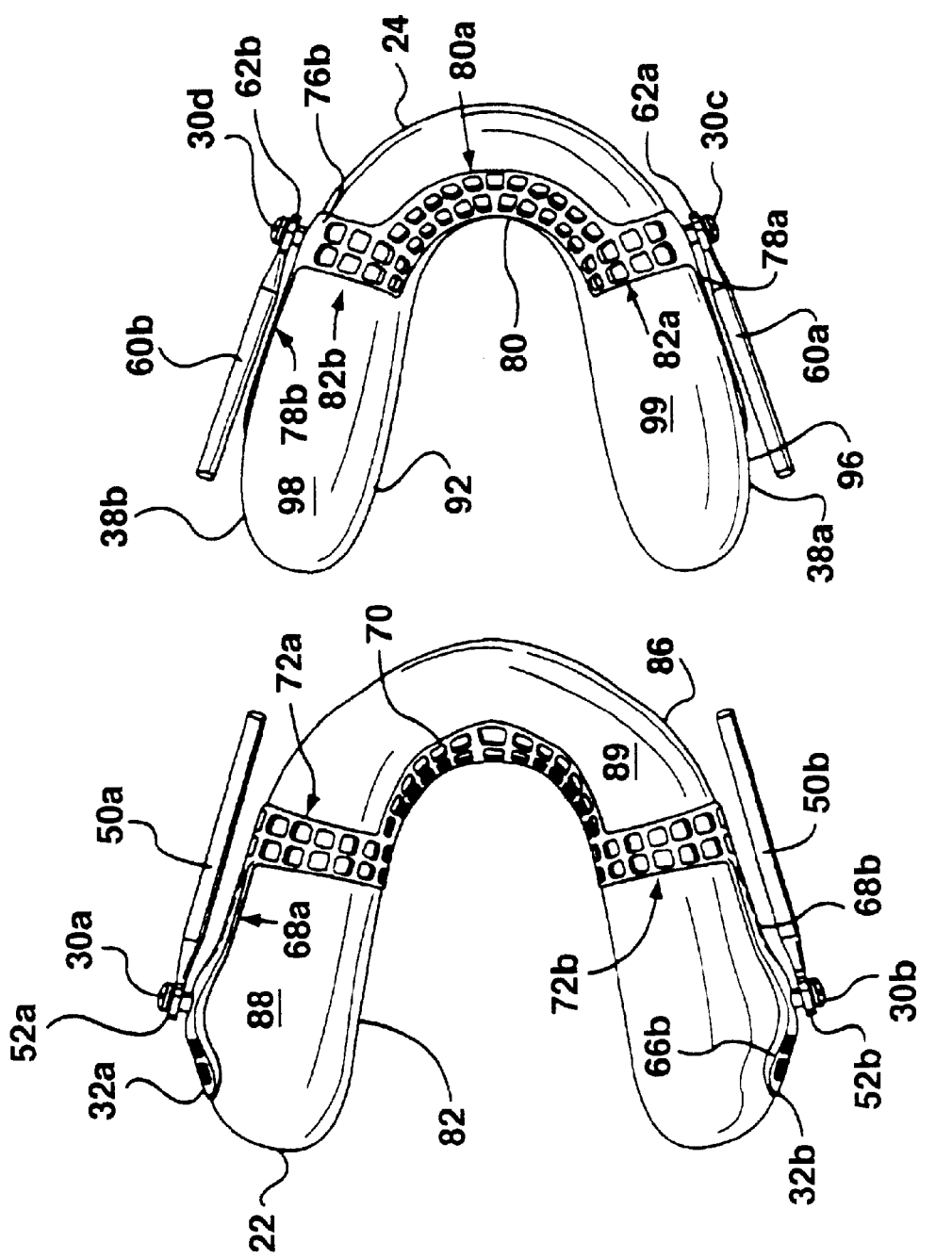
FIG. 2 is a plan view of the device of FIG. 1 with the bite forms separated.

Turning to FIGS. 1 and 2, an anti-snoring device 20 has a maxillary bite form 22 and a mandibular bite form 24. Each bite form may be fabricated of acrylic and has a dentition receiving cavity 26 which reflects the dentition of the intended user of the device. The dentition receiving cavity 26 may be lined with a soft fabric.

Two outwardly extending maxillary pivots 30a, 30b are posteriorly located on opposite sides 32a, 32b of the maxillary bite form 22. The pivot center of each of these maxillary pivots 30a, 30b may be located between the mesial of the first molar and the mesial of the second molar mirrored by the maxillary bite form 22. Two outwardly extending mandibular pivots 30c, 30d are anteriorly located on opposite sides 38a, 38b of the mandibular bite form 24. The pivot center of each of the mandibular pivots 30c, 30d may be located posteriorly of the distal edge of the cuspid mirrored by the mandibular bite form.

Figure 3:
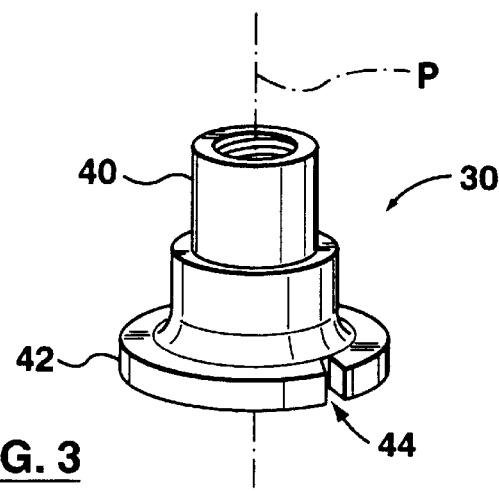
FIG. 3 is a top and side view of a pivot in the device of FIG. 1, FIGS. 4 and 5 are perspective views of jigs used in constructing the device of FIG. 1.

Referencing FIG. 3, each pivot 30 has an interiorly threaded cylindrical pivot portion 40 with a pivot axis P and an enlarged cylindrical base 42 with a notch 44. (Typically, the pivot is manufactured with a cylindrical base and the notch is cut out later.) Returning to FIGS. 1 and 2, a sleeve 50a terminates in an eyelet 52a which is pivotably mounted on maxillary pivot 30a. A screw 54a threaded to pivot 30a retains the eyelet on the pivot 30a. Similarly, eyelet 52b of sleeve 50b is pivotably mounted on pivot 30b and retained by a screw. A rod 60a terminates in an eyelet 62a which is pivotably mounted on mandibular pivot 30c. A screw threaded to pivot 30c retains the eyelet on the pivot 30c. Similarly, eyelet 62b of rod 60b is pivotably mounted on pivot 30d and retained by a screw. Each sleeve 50a, 50b telescopingly receives a respective rod 60a, 60b to form a telescoping arm 63a, 63b pivoted at either end to a maxillary pivot and to a mandibular pivot. The eyelets have a larger interior diameter than the outer diameter of the cylindrical pivot portion 40 of the pivots 30 so that pivotable connections are loose (i.e., they allow for some play).

A maxillary mesh framework 64, fabricated of metal, is at least partially embedded in the maxillary bite form 22. Framework 64 has pivot mounts 66a, 66b (FIG. 9) for maxillary pivots 30a, 30b. Each pivot mount is an opening through the mesh sized to accommodate the cylindrical pivot portion 40 of a pivot 30 but which is substantially smaller than the enlarged base 42 of the pivot. Similarly, a mandibular mesh framework 74 is at least partially embedded in the mandibular bite form 24 and has pivot mounts 76a, 76b (FIG. 9) for mandibular pivots 30c, 30d.

Maxillary mesh framework 64 has a first portion 68a embedded in the buccal face 86 of the maxillary bite form 22 at side 32a. This first portion has pivot mount 66a. Framework 64 also has a second portion 68b embedded in buccal face 86 of form 22 at side 32b; this second portion has pivot mount 66b. A medial portion 70 of framework 64 is embedded in a lingual face 82 of the maxillary bite form 22. A first bridge 72a extends across an occlusal face 88 of the maxillary bite form 22 and joins the first portion 68a with the medial portion 70. Similarly, a second bridge 72b extends across occlusal face 88 of the maxillary bite form and joins the second framework portion 68b with medial portion 70.

The first bridge 72a and the second bridge 72b are located at dentition mirrored by the maxillary bite form 22 which has a lower height than other dentition mirrored by the form. Typically, this means that the bridges are located somewhere between the distal of the 3's (i.e., the cuspids)) mirrored by the form or at the mesial of the 6's (i.e., the first molars) mirrored by the form.

In a similar fashion, mandibular mesh framework 74 has a first portion 78a embedded in the buccal face 96 of the mandibular bite form 24 at side 38a. This first portion has pivot mount 76a. Framework 74 also has a second portion 78b embedded in buccal face 96 of form 24 at side 38b; this second portion has pivot mount 76b. A medial portion 80 of framework 74 is embedded in a lingual face 92 of the mandibular bite form 24. A first bridge 82a extends across an occlusal face 98 of the mandibular bite form 24 and joins the first portion 78a with the medial portion 80. Similarly, a second bridge 82b extends across occlusal face 98 of the maxillary bite form and joins the second framework portion 78b with medial portion 80.

Again, the bridges 82a, 82b are located at dentition mirrored by the mandibular bite form 24 which has a lower height than other dentition mirrored by the form.

The occlusal face 88 of the maxillary bite form 22 has a central planar portion 89 which is in registration with a central planar portion 99 of the occlusal face 98 of the mandibular bite form 24. These planar portions 89, 99 meet when the device 20 is closed. Further, these planar portions parallel a bite plane of the dentition.

In operation, a user whose dentition is mirrored by the bite forms 22, 24 may insert the bite forms in his mouth and bite down to seat the bite forms on his dentition. The telescoping arms 63a, 63b allow the user to open and close his mouth. Further, the loose pivot connection between these arms 63a, 63b and pivots 30a to 30d allow the user some lateral freedom (to brux). However, when the user closes his mouth such that the two bite forms abut, the arms maintain the mandibular bite form 24, and hence the users mandible, in a position which juts forward of the user's maxilla. This avoids constriction of the user's throat and hence alleviates snoring and sleep apnea.

The positioning of pivots 30a, 30b between the first and second molars of the maxilla and the positioning of pivots 30c, 30d at the cuspids of the mandible assist in relieving stress on the temporal mandibular joint (TMJ) during bruxing. Further in this regard, the central planar portions 89, 99 of the occlusal faces 88, 98 of the bite forms 22, 24, which meet when the forms are closed and mirror the bite plane of the user, also relieve stress on the TMJ during bruxing.

The mesh frameworks 64, 74 with their pivot mounts 66a, 66b and 76a, 76b, respectively, provide an enduring mount for pivots 30a to 30d. More particularly, even in the face of extensive bruxing, the pivots 30a to 30d will not pull out of the metal mesh frameworks 64, 74 and the mesh frameworks, being embedded in a significant portion of the bite frames 22, 24, also will not pull out. Further, the medial portion of framework 74 acts to strengthen the medial portion of the mandibular bite form 24. This is beneficial since this portion of the bite form is subject to stress during bruxing which, absent the framework, could result in a stress fracture.

To manufacture the device 20 of FIG. 1, impressions are taken of a patient's dentition and maxillary and mandibular master casts 130, 132 (FIG. 7) are fabricated from these impressions. The master casts are then mounted to an articulator 134 (FIG. 7) which is adjusted so as to establish the proper closed position of the two master casts. As will be appreciated by those skilled in the art, this may be accomplished with a George gauge which allows the determination of the proper protruded position of the mandibular cast with respect to the maxillary cast and the minimum vertical spacing between the casts. Vent holes may then be drilled into these casts. A dual laminate material may then be attached (with heat) to the dentition of the master casts such that the harder layer of the laminate is on the outside.

Figure 4:
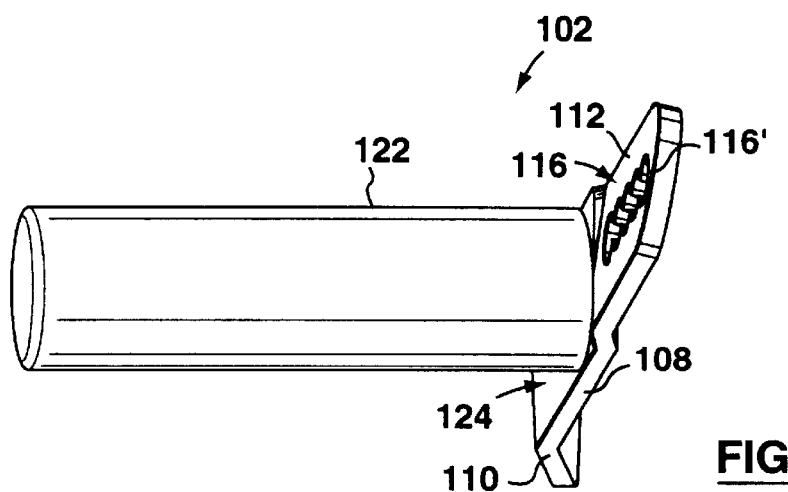
Figure 5:
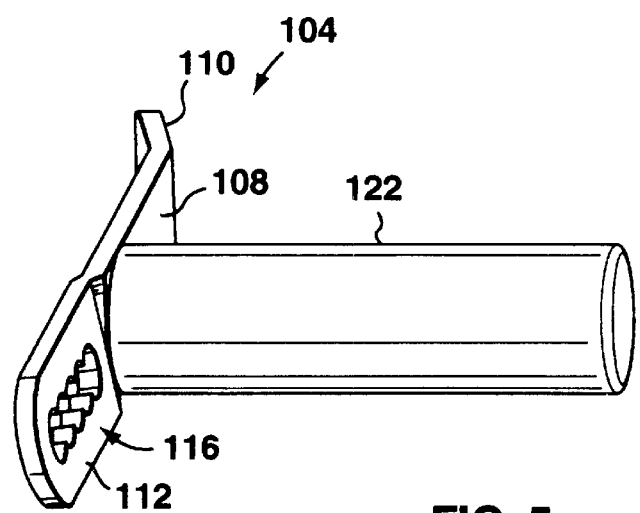
Figure 6:
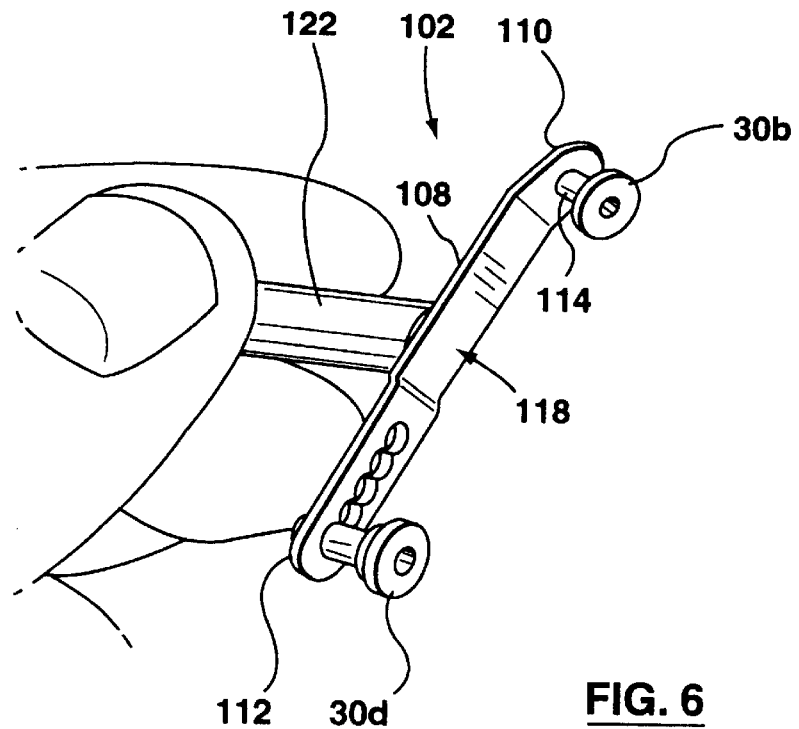
FIG. 6 is a perspective view of the jig of FIG. 4 shown in use.

Next the pivots 30a to 30d are located on the master casts. With reference to FIGS. 4 to 6, to facilitate this, left and right jigs 102, 104, respectively, are used. Each jig has a medial portion 108 and two end portions 110, 112. End portion 110 has a single through bore 114 which acts as a pivot receptor while end portion 112 has a plurality of aligned through bores (pivot receptors) 116 along its length. End portion 110 is bent inwardly so that its pivot receptor 114 cants toward inward face 118 of medial portion 108 at an angle of about 15 degrees. End portion 112 is twisted with respect to the medial portion 108 such that pivot receptors 116 cant downwardly on the inward side 120 of the jig at an angle of about seven degrees. A handle 122 extends from the outward side 124 of the jig. The canting of the pivot receptors assist in ensuring that the jig will place the pivots at an angle which is mirrored by the dentition so that the inner surface of the pivots is substantially flush with the dentition.

Referencing FIG. 6, the pivot portion 40 of a pivot 30b is pushed into receptor 114 of jig 102 from the inward side 120 of the jig and a screw is threaded into the pivot portion from the outward side 124 of the jig in order to secure the pivot 30b to the jig. A pivot 30d is pushed in to the receptor 116'

(FIG. 4) which is closest to the outer end of end portion 112 from the inward side of the jig and another screw is threaded to the pivot to secure it to the jig. Similarly, pivots 30a and 30c are secured to jig 104.

Figure 7:
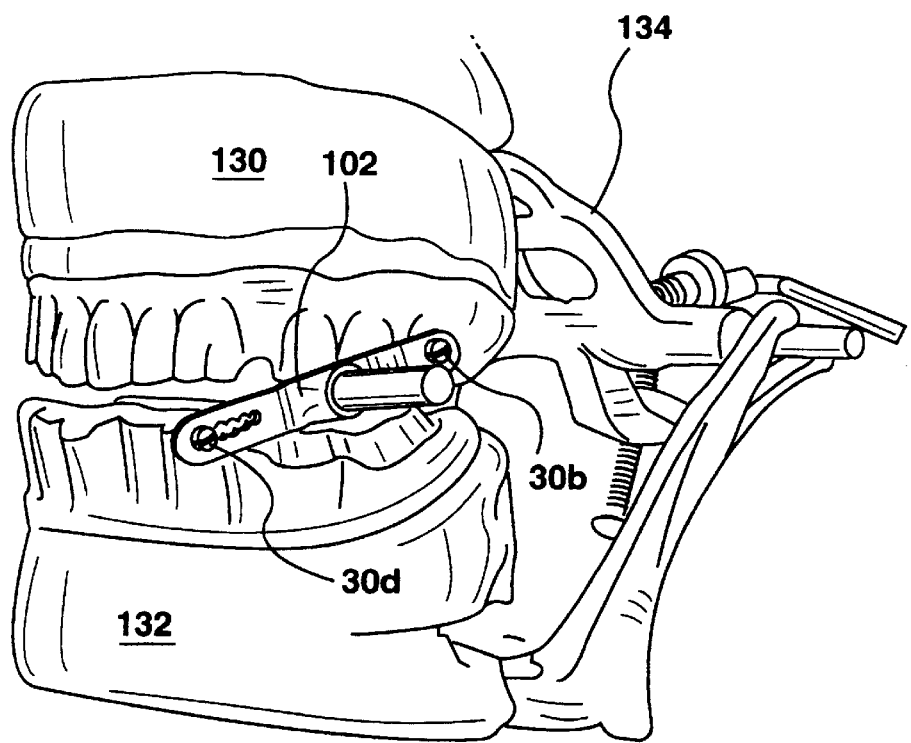
FIG. 7 is a perspective view of master casts in an articulator showing the jig of FIG. 4 in use.

Turning to FIG. 7, the left jig 102 may then used to locate the pivots 30b, 30d, as follows. First pivot 30b in receptor 114 (FIG. 6) is located by placing its center P (FIG. 3) interproximal to the first and second molars on the left side of the maxillary cast 130. Preferably, the center of the pivot is not located posteriorly of the mesial of the second molar to avoid the pivot impinging on the muscles of a user of a device 20 (FIG. 1) and causing discomfort. Ideally, the pivot should be centered between the occlusal cusps and the gingival margin of the molars. However, where due to a short crown, the pivot, so located, would extend past the occlusal edge of the molars, the pivot should be moved toward the tissue even if this means extending past the gingival margin. If this is not done, it may weaken device 20 (FIG. 1).

Next, while holding pivot 30b in its correct location, the jig 102 is manipulated to locate pivot 30d appropriately. Ideally, pivot 30d is located in the center of the dentition between the occlusal/incisal edge and the gingival margin. However, again, the pivot should not extend past the occlusal/incisal edge and may, if necessary, be located partially on the tissue surface. Preferably, the center of the pivot 30d is not located anteriorly of the distal edge of the lower cuspid as this may cause discomfort to the lower lip and may also reduce the amount of lateral movement of the device 20 (FIG. 1). If the jig does not so locate the pivot, pivot 30d should be placed in another of pivot receptors 116 (FIG. 4) so that the pivot may be properly located. The pivots may then be secured in position using hot wax. This same procedure may then be used with jig 104 to locate pivots 30a and 30c.

The pivots are ideally located at the same position at either side of the casts in order to maximize the lateral movement which will be permitted by the device 20 (FIG. 1) when bruxing thus helping to reduce stress on the TMJ.

With the pivots correctly located and secured to the casts, the screws retaining them to the jigs may be removed and the jigs taken away. The wax around the base of the pivots may then be trimmed and the pivots then pulled off leaving an indentation in the remaining wax marking their proper locations. The casts are then removed from the articulator.

Next duplicating pivots 140 (FIG. 8) are placed into the wax indentations and secured in place. A mould is then taken of each cast 130, 132; framework fabrication casts 230, 232 (FIG. 9) are made from these moulds. Frameworks 64, 74 are then cast from molten metal using these fabrication casts and conventional casting processes. The castings are designed so that the frameworks meet the following criteria. The first and second portions 68a, 68b of the maxillary framework 64 ideally start at the distal of the 7's and continue along the buccal face of the posterior teeth until bridges 72a, 72b. The medial portion 70 of the framework extends along the lingual face of the teeth between the bridges. The first and second portions 78a, 78b of the mandibular framework ideally start at the mesial of the 3's and continue past the bridge 82a, 82b to the distal of the 6's.

These bridges should be located where they will not interfere with the occlusal plane, thus, in an area where the dentition is lower in height than the rest of the dentition, as aforenoted. A thin protuberance 150, 160 on each framework 64, 74 extends posteriorly directly behind the centrals.

Figure 10:
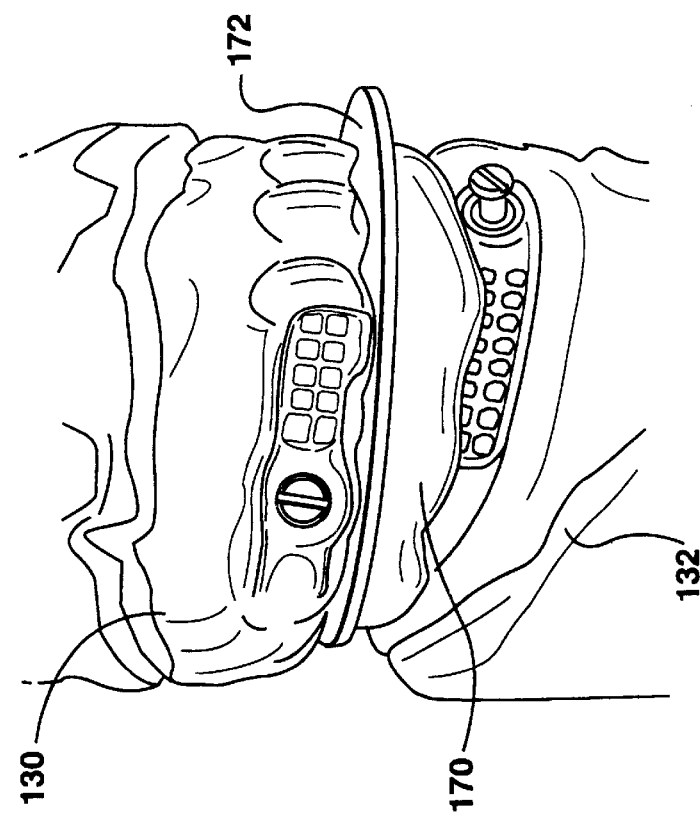
FIG. 10 is a perspective view of the master casts of FIG. 7 with the frameworks of FIG. 9 and a twenty-degree bite plate.

After casting the frameworks, they are removed from the fabricating casts and pivots 30 are inserted into the pivot mounts of the frameworks. The duplicating pivots are removed from the master casts 130, 132 (FIG. 7) and the frameworks, carrying the pivots 30, are then positioned on the casts 130, 132. The casts are then re-mounted to the articulator 134 (FIG. 7). With the articulator in its closed position, the gap (G—not shown) is measured between the upper and lower incisal edges of the dentition at the anterior midline and the closing limit of the articulator to establish this gap is noted. Referencing FIG. 10, a warm (and hence pliable) wax body 170 is then applied over the dentition of the mandibular cast 132. This wax body is manipulated so as not to cover the pivots 30c, 30d (FIG. 2) or the protuberance 160 (FIG. 9) of framework 74 and to at least partially embed framework 74. A twenty degree bite plate 172 is held evenly against the dentition of the maxillary cast and the articulator is closed until the plate makes an even contact with the wax body and just touches any part of the dentition of the mandibular cast. The anterior midline of the bite plate is aligned with the midline of the anterior teeth. Further, the posterior portion of the bite plate is symmetrically positioned with respect to the posterior teeth. The bite plate is then secured to the wax body 170 (with a warm wax instrument) as seen in FIG. 10.

The closing limit of the articulator 134 (FIG. 7) is then adjusted to establish a gap (G/2) between the lower incisal edges of the dentition of the maxillary cast 130 at the anterior midline and the twenty degree bite plate 172. This gap is equal to one half the gap (G) previously measured between the upper and lower incisal edges of the dentition at the anterior midline.

Figure 11:
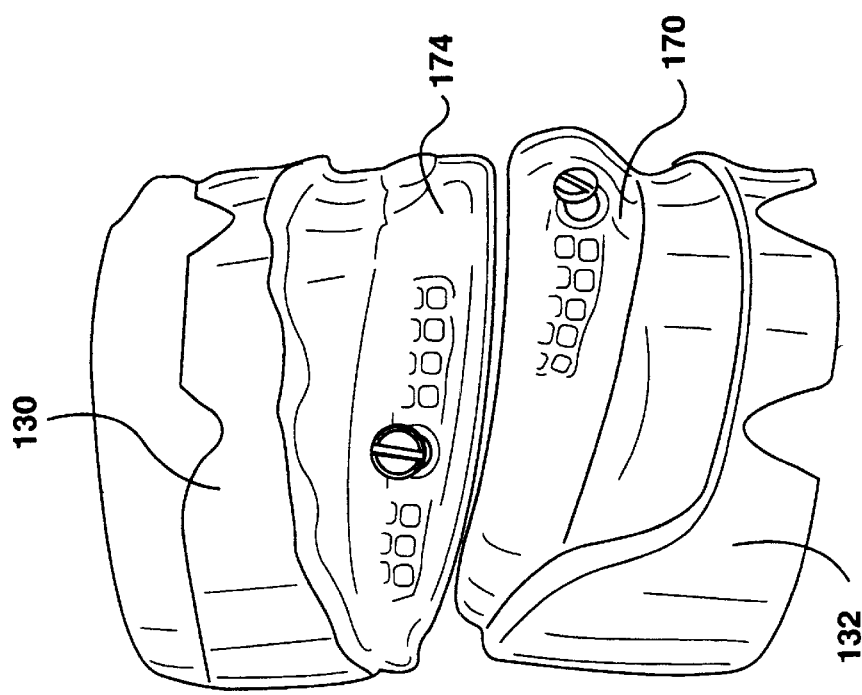
FIG. 11 is a perspective view of the master casts of FIG. 7 with the frameworks of FIG. 9 and wax bodies.

The articulator is then opened and a wax body 174 (FIG. 11) is applied over the dentition of the maxillary cast. Again, the wax body is manipulated so as not to cover the pivots 30, 30b (FIG. 2) or protuberance 150 (FIG. 9) and at least partially embed framework 64. The articulator is again moved toward a closed position while laterally reciprocating the casts in order that the twenty-degree bite plate 172 smooths and angles an occlusal surface of the maxillary wax body. Once the articulator has bottomed out on the closing limit, the shaping of the maxillary wax body is complete and the twenty-degree bite plate may then be removed. The closing limit of the articulator is then re-adjusted to the position that reflected the gap (G) between the upper and lower incisal edges of the dentition of the casts at the anterior midline. Then, with the upper wax body cooled and hard and the lower wax body slightly warm and pliable, the articulator is again moved toward a closed position while the casts are laterally reciprocated. This results in the maxillary wax body smoothing and angling the mandibular wax body. This stage of the procedure is illustrated in FIG. 11.

Figure 12:
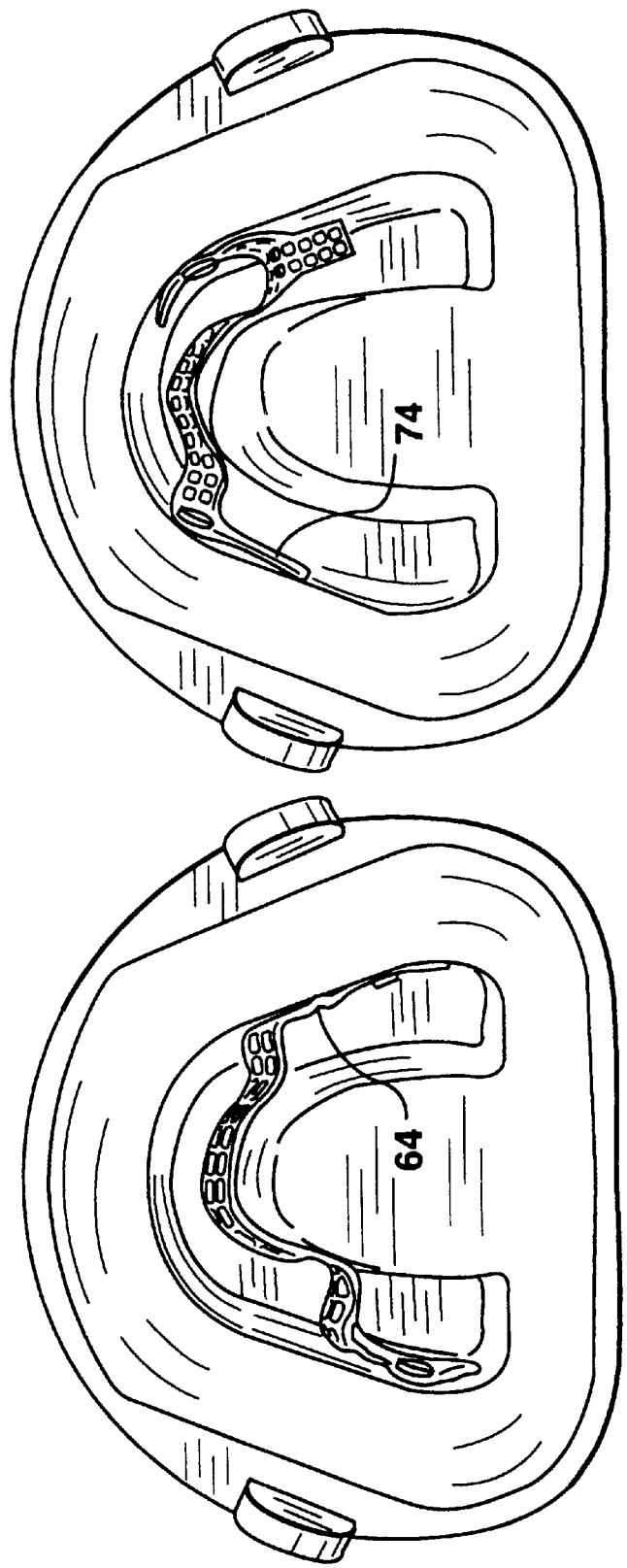
FIG. 12 is a top view of mould cavity halves with the frameworks of FIG. 9.

The master casts 130, 132 are then removed from the articulator and a mould forming material (such as plaster) is applied around each wax body 170, 174 such that each protuberance 150, 160 (FIG. 9) and pivots 30a to 30d are embedded in the mould forming material. The mould forming material is then allowed to set. Subsequently, heat is applied to melt the wax so that the wax can be removed. This leaves mould forming cavities. FIG. 12 illustrates one half of each of these mould forming cavities with the maxillary and mandibular casts removed for illustration purposes. The embedding of the protuberances and pivots is apparent from FIG. 12. Each mould cavity may then be filled with a curable material, such as acrylic. The embedded protuberances and pivots anchor the frameworks 64, 74 in proper position during this process. After the curable material has hardened, it forms the maxillary and mandibular bite forms 22, 24 seen in FIG. 1 with the at least partially embedded frameworks.

The maxillary and mandibular casts may then be removed, leaving behind the dual laminate which is now firmly embedded on the occlusal surface of the bite forms with the soft layer of the laminate exposed. The hardened moulding material may then be broken away from the bite forms. Next the rods and sleeves may can be attached to appropriate pivots with screws and the device 20 described in conjunction with FIG. 1 completed. In this regard, the notch 44 (FIG. 3) in the embedded base 42 of the pivots prevents the pivots from turning while the screws are turned.

Modifications will be apparent and, therefore, the invention is defined in the claims.

What is claimed is:

1. An anti-snoring device, comprising:

a maxillary bite form;

a mandibular bite form;

a first outwardly extending maxillary pivot posteriorly located on a first side of said maxillary bite form;

a second outwardly extending maxillary pivot posteriorly located on a second side of said maxillary bite form;

a first outwardly extending mandibular pivot anteriorly located on a first side of said mandibular bite form;

a second outwardly extending mandibular pivot anteriorly located on a second side of said mandibular bite form;

a first telescoping arm loosely pivoted to said first maxillary pivot and to said first mandibular pivot;

a second telescoping arm loosely pivoted to said second maxillary pivot and to said second mandibular pivot;

maxillary framework at least partially embedded in said maxillary bite form having a pivot mount for said first maxillary pivot and a pivot mount for said second maxillary pivot;

mandibular framework at least partially embedded in said mandibular bite form having a pivot mount for said first mandibular pivot and a pivot mount for said second mandibular pivot.

2. The anti-snoring device of claim 1 wherein said maxillary framework has a first portion extending along said first side, a second portion extending along said second side, and a medial portion joining said first portion and said second portion.

3. The anti-snoring device of claim 2 wherein said first portion and said second portion are embedded in a buccal face of said maxillary bite form and said medial portion is embedded in a lingual face of said maxillary bite form and wherein said maxillary framework has a first bridge extending across an occlusal face of said maxillary bite form joining said first portion with said medial portion and a second bridge extending across said occlusal face of said maxillary bite form joining said second portion with said medial portion.

4. The anti-snoring device of claim 3 wherein said first bridge and said second bridge are located at dentition mirrored by said maxillary bite form which has a lower height than other dentition mirrored by said maxillary bite form during use.

5. The anti-snoring device of claim 3 wherein said first bridge and said second bridge are located between a distal of 3's (cuspids) and a mesial of 6's (first molars) mirrored by said maxillary bite form during use.

6. The anti-snoring device of claim 3 wherein each said pivot has a cylindrical pivot portion and an integrally formed enlarged base portion.

7. The anti-snoring device of claim 6 wherein said enlarged base portion is configured as a notched cylinder.

8. The anti-snoring device of claim 1 wherein a pivot center of each of said first and second maxillary pivots is located at a point between a distal of a first molar and a mesial of a second molar mirrored by said maxillary bite form during use.

9. The anti-snoring device of claim 8 wherein a pivot center of each of said first and second mandibular pivots is located posteriorly of a distal edge of a cuspid mirrored by said mandibular bite form whereby stress on a temporal mandibular joint is reduced during bruxing.

10. The anti-snoring device of claim 1 wherein an occlusal face of said maxillary bite form has a central planar portion which mirrors a bite plane of dentition reflected by said maxillary bite form and said mandibular bite form and wherein an occlusal face of said mandibular bite form has a central portion which mirrors said bite plane during use.

* * * * *